(12) United States Patent
Nakanishi

(10) Patent No.: US 10,029,051 B2
(45) Date of Patent: Jul. 24, 2018

(54) INFUSION PUMP

(71) Applicant: Terumo Kabushiki Kaisha, Tokyo (JP)

(72) Inventor: Masaru Nakanishi, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 173 days.

(21) Appl. No.: 14/618,778

(22) Filed: Feb. 10, 2015

(65) Prior Publication Data

US 2015/0151057 A1    Jun. 4, 2015

Related U.S. Application Data

(63) Continuation of application No. PCT/JP2012/005124, filed on Aug. 10, 2012.

(51) Int. Cl.
| | | |
|---|---|---|
| *A61M 5/36* | (2006.01) | |
| *A61M 5/142* | (2006.01) | |
| *A61M 5/162* | (2006.01) | |
| A61M 5/168 | (2006.01) | |

(52) U.S. Cl.
CPC ........ *A61M 5/365* (2013.01); *A61M 5/14228* (2013.01); *A61M 5/162* (2013.01); *A61M 5/142* (2013.01); *A61M 2005/16868* (2013.01); *A61M 2005/16872* (2013.01); *A61M 2205/3375* (2013.01)

(58) Field of Classification Search
CPC .. A61M 5/142; A61M 5/14228; A61M 5/365; A61M 2005/16868; A61M 2005/16872; A61M 2205/3375; A61M 1/3626; F04B 43/082; F04B 43/084
See application file for complete search history.

(56) References Cited

U.S. PATENT DOCUMENTS

| 5,489,265 A | * | 2/1996 | Montalvo | ............. A61M 5/365 |
| | | | | 604/67 |
| 2006/0140798 A1 | | 6/2006 | Kutsuzawa | |
| 2008/0098798 A1 | * | 5/2008 | Riley | ................... A61M 5/365 |
| | | | | 73/19.03 |

FOREIGN PATENT DOCUMENTS

| EP | 1535637 A1 * | 6/2005 | ........ A61M 5/14228 |
| JP | 01-198560 A | 8/1989 | |
| JP | 05-305141 A | 11/1993 | |
| JP | 2010-508518 A | 3/2010 | |
| JP | 2010-200775 A | 9/2010 | |

(Continued)

OTHER PUBLICATIONS

The Extended European Search Report issued in Application No. 12882726.8 dated Apr. 11, 2016.

(Continued)

*Primary Examiner* — Bhisma Mehta
*Assistant Examiner* — Larry R Wilson
(74) *Attorney, Agent, or Firm* — Foley & Lardner LLP

(57) ABSTRACT

An infusion pump includes: a main body; a tube attachment section inside the main body; a liquid feed driving unit inside the main body; an access cover mounted on the main body and for covering the infusion tube when the infusion tube is attached to the tube attachment section when closed; and a bubble detection unit for detecting a bubble inside the infusion tube when the infusion tube is attached to the tube attachment section. The bubble detection unit includes a first member at the access cover and a second member at the main body.

11 Claims, 8 Drawing Sheets

(56) References Cited

FOREIGN PATENT DOCUMENTS

| JP | 2012-029915 A | 2/2012 |
|----|---------------|--------|
| WO | WO-2008/051998 A2 | 5/2008 |

OTHER PUBLICATIONS

International Search Report dated Sep. 18, 2012 issued in Application No. PCT/JP2012/005124.
Written Opinion of the International Searching Authority dated Sep. 18, 2012 issued in Application No. PCT/JP2012/005124.

* cited by examiner

H1 > H2

EMBODIMENT OF PRESENT INVENTION

Prior Art

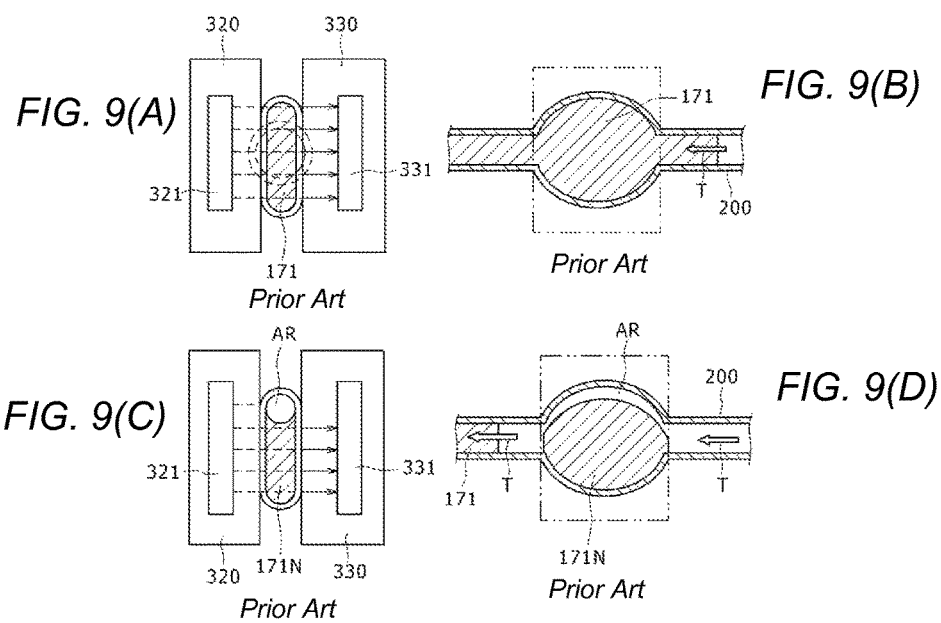

INFUSION PUMP

CROSS-REFERENCE TO RELATED APPLICATIONS

This application is a continuation application filed under 35 U.S.C. 111(a) claiming the benefit under 35 U.S.C. §§ 120 and 365(c) of PCT International Application No. PCT/JP2012/005124 filed on Aug. 10, 2012, the entire content of which is hereby incorporated by reference in its entirety.

BACKGROUND

Technical Field

The present disclosure relates to an infusion pump for feeding medicinal solution and the like to a patient. Particularly, the present disclosure relates to the infusion pump in which an infusion tube is attached to the infusion pump in a horizontal direction to feed liquid.

Background Art

An infusion pump is used in, for example, an intensive care unit (ICU) or the like, and applied to feed medicinal solution to a patient for a relatively long period with high accuracy. A predetermined medicinal solution bag (infusion bag) is disposed above the infusion pump. An infusion tube hung from the medicinal solution bag is sandwiched between a main body and an access door, and the infusion tube is housed inside the main body and held by closing the access door. Inside the main body of the infusion pump, an outer peripheral surface of the infusion tube set at a predetermined position is sandwiched between a plurality of fingers inside the main body and an inner surface of the access door. A peristaltic infusion pump is configured to feed the medicinal solution by sequentially pressing the outer peripheral surface of the infusion tube with the plurality of fingers along a length direction by individually driving the plurality of fingers of a liquid feed driving unit (e.g., refer to JP 2010-200775 A).

According to the infusion pump disclosed in JP 2010-200775 A, the infusion tube is held being vertically passed through the inside of the main body of the infusion pump from above downward. In contrast, there is a proposed infusion pump in which an infusion tube is held being horizontally passed through the inside of a main body of the infusion pump. A reason for adopting such a configuration in which the infusion tube is held being horizontally passed through the inside of the main body of the infusion pump is so that the infusion tube is not obstructive even when a plurality of infusion pumps is held in a state vertically stacked. This is different from the infusion pump in which the infusion tube is vertically passed through the inside of the main body of the infusion pump from above downward. For example, an upstream side of the infusion tube is set at a right-side portion when a person faces the main body of the infusion pump and a downstream side of the infusion tube is set at a left-side portion when a person faces the main body of the infusion pump. In this case, the medicinal solution can be fed from the upstream side to the downstream side in a predetermined feeding direction and can be correctly fed to a patient by driving the liquid feed driving unit when the upstream side of the infusion tube is set at the right-side portion of the main body of the infusion pump and the downstream side of the infusion tube is set at the left-side portion of the main body of the infusion pump.

An infusion pump includes a bubble detection unit (bubble sensor) configured to detect whether a bubble exists inside the infusion tube. The bubble sensor includes an ultrasonic transmitting unit and an ultrasonic receiving unit. In a type of the infusion pump where an infusion tube is held being vertically passed through the inside of a main body of the infusion pump, when a boundary between medicinal solution and air (bubble) passes a portion where a flow path of the infusion tube is narrowed at the bubble sensor, the medicinal solution directly flows downward in a state such that the liquid surface of the medicinal solution is spread over an entire part of the portion where the flow path of the infusion tube is narrowed.

In contrast, in a type of the infusion pump where the infusion tube is held being horizontally passed through the inside of a main body of the infusion pump, when the boundary between the medicinal solution and the air (bubble) passes the portion where the flow path of the infusion tube is narrowed at the bubble sensor, the medicinal solution (also referred to as droplet of the medicinal solution) is partly caught at an inner surface of the portion where the flow path of the infusion tube is narrowed, and the medicinal solution may partly remain inside the portion where the flow path of the infusion tube is narrowed because of influences from surface tension of the medicinal solution and gravity.

When the medicinal solution thus partly remains inside the portion where the flow path of the infusion tube is narrowed, ultrasonic from the ultrasonic transmitting unit of the bubble sensor is transmitted through a part of the remaining medicinal solution and received by the ultrasonic receiving unit. Due to this, the bubble sensor may determine that the medicinal solution exists inside the infusion tube and erroneously detects that there is no bubble although the bubble actually exists inside the infusion tube.

SUMMARY OF THE INVENTION

Considering the problem above, one objective of certain embodiments of the present invention is directed to providing an infusion pump capable of preventing the bubble sensor from erroneously detecting existence of the bubble by preventing the medicinal solution from partly remaining inside the portion where the flow path of the infusion tube is narrowed by the bubble sensor.

An infusion pump according to certain embodiments of the present invention includes: a main body; a tube attachment section disposed inside the main body, where an infusion tube configured to feed medicinal solution to a patient side is attached in a horizontal direction (lateral direction); a liquid feed driving unit disposed inside the main body and configured to feed the medicinal solution inside the infusion tube in a lateral direction by pressing the infusion tube in a state that the infusion tube is attached to the tube attachment section; an access cover mounted on the main body and configured to cover the infusion tube attached to the tube attachment section by being closed; and a bubble detection unit configured to detect a bubble inside the infusion tube attached to the tube attachment section, wherein the bubble detection unit includes a first member disposed at the access cover and having an ultrasonic transmitting unit, a second member disposed at the main body and having an ultrasonic receiving unit configured to receive ultrasonic from the ultrasonic transmitting unit, and a second space to narrow a flow path of the infusion tube on a more downstream side than the bubble detection unit of the infusion tube, the second space being set smaller compared to a first space to narrow the flow path of the infusion tube between the first member and the second member in a state that the access cover is closed.

According to the above-described configuration, the second space to narrow the flow path of the infusion tube on the more downstream side than the bubble sensor is set smaller compared to the first space to narrow the flow path of the infusion tube between the first member and the second member. Therefore, a stagnation phenomenon at a liquid stagnant portion of the medicinal solution can be generated on the downstream side of the bubble sensor instead of between the members of the bubble sensor. This is because surface tension of the medicinal solution tends to break at a portion where a flow rate of the medicinal solution rapidly changes. Therefore, the bubble sensor is prevented from erroneously detecting the liquid stagnant portion because the so-called liquid stagnant portion of the medicinal solution is not left out between the first member and the second members of the bubble sensor. Therefore, the bubble sensor can be prevented from erroneously detecting the existence of the bubble by avoiding a part of the medicinal solution remaining inside the portion where the flow path of the infusion tube is narrowed by the bubble sensor.

In one aspect, the first member includes a base portion, a projecting curved surface portion formed in a projecting manner from the base portion, and a projecting portion formed in a projecting manner on the more downstream side than the projecting curved surface portion to set the second space, and the second member includes a projecting curved surface portion facing the projecting curved surface portion of the first member and configured to set the first space.

With this configuration, the projecting portion to set the second space is integrally formed with the first member, and therefore, the number of components can be reduced compared to a case where the projecting portion is separately provided from the first member.

In one aspect, a projecting height of the projecting portion from the base portion of the first member is set higher than a projecting height of the projecting curved surface portion from the base portion.

With this configuration, the second space formed by the projecting portion can be set smaller than the first space of the bubble sensor only by disposing the first member.

In one aspect, a display unit and an operation panel are disposed at an upper portion of the main body, and the tube attachment section, the liquid feed driving unit, and the access cover are disposed at a lower portion of the main body.

With this configuration, a medical staff can attach the infusion tube to the tube attachment section while confirming information on the display unit at the upper portion of the main body, and then can close the access cover. Further, the medical staff can operate the operating buttons at the operation panel while confirming the information on the display unit at the upper portion of the main body cover.

Certain embodiments of the present invention can provide an infusion pump capable of preventing a bubble sensor from erroneously detecting a bubble by avoiding a last part of administered medicinal solution remaining inside a portion where a flow path of an infusion tube is narrowed by the bubble sensor.

BRIEF DESCRIPTION OF THE DRAWINGS

FIG. 9(A) is a side view diagram illustrating a state in which a liquid stagnant portion of the medicinal liquid is not generated when a flow path of the infusion tube is narrowed by the infusion tube by being pressed by the bubble sensor in the related art.

FIG. 9(B) is a front view of the state shown in FIG. 9(A).

FIG. 9(C) is a side view diagram illustrating a state in which the liquid stagnant portion is generated when a flow path of the infusion tube is narrowed by the infusion tube by being pressed by the bubble sensor in the related art.

FIG. 9(D) is a front view of the state shown in FIG. 9(C).

DETAILED DESCRIPTION

In the following, a preferred embodiment of the present invention will be described in detail with reference to accompanying drawings.

Note that the embodiment described below contains various technical preferred limitations for being a preferable example of the present invention, but a technical scope of the present invention is not limited thereto unless otherwise particularly specified to limit the present invention in the following description.

Figure 1:
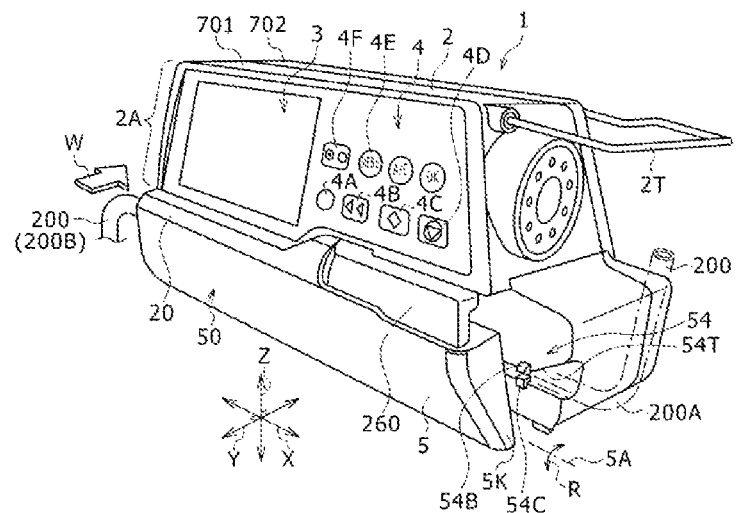
FIG. 1 is a front-side perspective view illustrating a preferred embodiment of an infusion pump according to the present invention.
Figure 2:
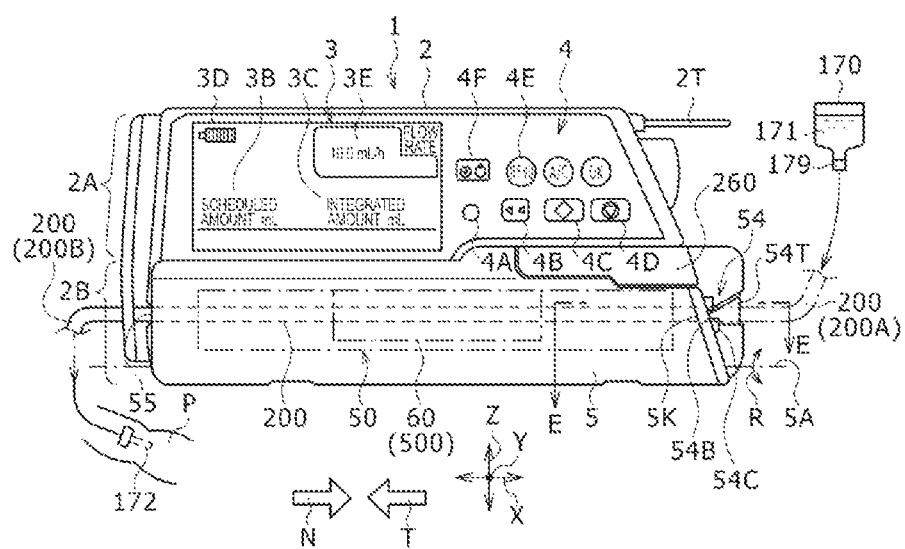
FIG. 2 is a perspective view illustrating the infusion pump illustrated in FIG. 1, viewed from W-direction.

FIG. 1 is a perspective view illustrating a preferred embodiment of an infusion pump according to the present invention. FIG. 2 is a perspective view illustrating the infusion pump illustrated in FIG. 1, viewed from W-direction.

An infusion pump 1 illustrated in FIGS. 1 and 2 is used, for example, in an intensive care unit (ICU, CCU, NICU) and the like, and is a continuous micro-injection pump used for injecting a micro amount of a medicinal solution, such as anticancer drugs, anesthetics, a chemotherapeutic agents, blood to be transfused, and nutritional supplements, to a patient with high accuracy for a relatively long time. The medicinal solution to be used is selected from a medicinal solution library, and the infusion pump 1 is used to feed the selected medicinal solution. The medicinal solution library is information of medicinal solutions which corresponds to administering setting groups of the medicinal solutions including names of medicinal solutions preliminarily registered in a medicinal solution library database (DB). A medical staff can select the medicinal solution and set the medicinal solution by using the medicinal solution library without executing complicated administration setting in each case.

As illustrated in FIG. 2, the infusion pump 1 can accurately feed liquid to a patient P from a medicinal solution bag 170 filled with medicinal solution 171 through a forceps 179, an infusion tube 200, and an intravenous cannula 172. The medicinal solution 171 is also referred to as infusion fluid. The infusion tube 200 is also referred to as an infusion line.

The infusion pump 1 includes a main body cover 2 and a handle 2T, and the handle 2T can be extended in N-direction and can be housed in a feeding direction T. The main body cover 2 is also referred to as a main body and is integrally formed from a molded resin material having chemical resistance. The main body cover 2 includes a splash proof structure whereby medicinal solution or the like can be prevented from entering the inside of the infusion pump 1 even when the medicinal solution or the like is splashed. The main body cover 2 is thus provided with the splash proof structure because there is possibility that medicinal solution 171 contained in the medicinal solution bag 170 disposed above spills, or disinfectant or the like used nearby splashes and adheres.

First, elements disposed at the main body cover 2 of the infusion pump 1 will be described.

As illustrated in FIGS. 1 and 2, a display unit 3 and an operation panel 4 are disposed at an upper portion 2A of the main body cover 2. The display unit 3 is an image display unit using, for example, a display unit of a color LCD. The display unit 3 can display information in the Japanese language or in in other languages as needed. The display unit 3 is located at an upper left position of the upper portion 2A of the main body cover 2, and disposed on an upper side of an access cover 5.

The upper portion 2A of the main body cover 2 is an upper half portion of the main body cover 2. A lower portion 2B of the main body cover 2 is a lower half portion of the main body cover 2. In FIG. 2, the display unit 3 displays, for example, a scheduled amount of medicinal solution administration (mL) at a display field 3B, an integrated amount of medicinal solution administration (mL) at a display field 3C, a charge history at a display field 3D, and a flow rate (mL) at a display field 3E, etc., but the display unit 3 illustrated in FIG. 1 omits these display contents for simplifying the drawing. The display unit 3 also can display a warning message besides the above-mentioned information.

The operation panel 4 is disposed on a right side of the display unit 3 at the upper portion 2A of the main body 2. According to the example in the drawing, a pilot lamp 4A, a fast feeding switch button 4B, a start switch button 4C, a stop switch button 4D, a menu select button 4E, a power switch button 4F, etc. are provided on the operation panel 4 as the examples of operation buttons.

As illustrated in FIG. 1, the access cover 5 is provided at the lower portion 2B of the main body cover 2 in an openable manner in R-direction, centering a rotary shaft 5A. The access cover 5 is the plate-like cover member formed in a long shape along the X-direction. A tube attachment section 50 and a liquid feed driving unit 60 are disposed on an inner side of the access cover 5. At the tube attachment section 50, the infusion tube 200 made of a flexible thermoplastic resin such as flexible polyvinyl chloride or the like is set, and the infusion tube 200 can be horizontally attached to the tube attachment section 50 in the X-direction (feeding direction T) by closing the access cover 5.

Note that the X-direction, the Y-direction, and the Z-direction in FIGS. 1 and 2 are orthogonal to one another, and the Z-direction is a vertical direction. The X-direction is parallel to the feeding direction T and corresponds to a lateral direction of the infusion pump 1. The Y-direction is a front-back direction of the infusion pump 1.

Figure 3:
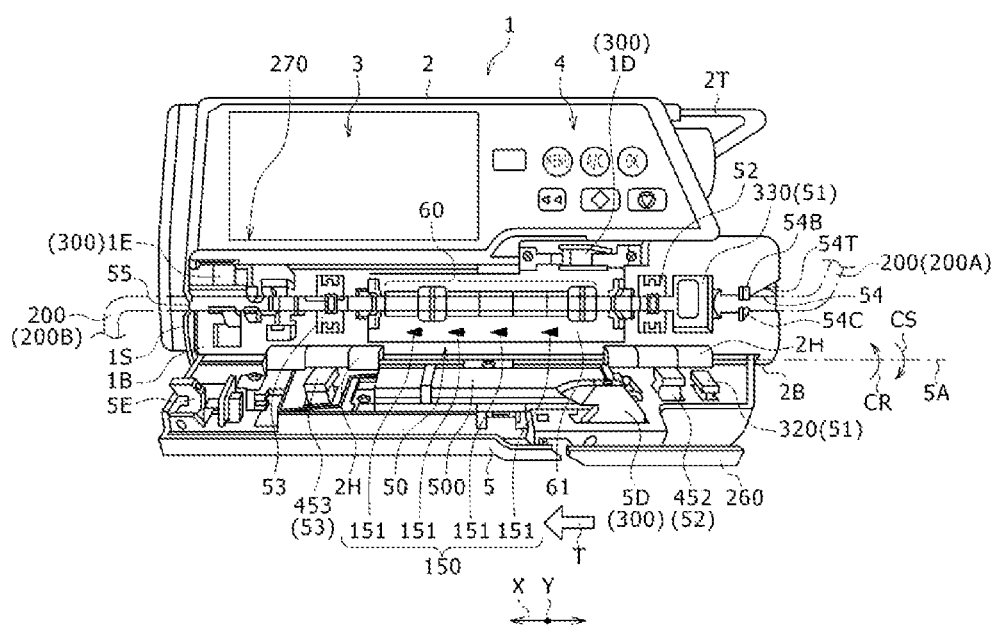
FIG. 3 is a perspective view illustrating a tube attachment section for attaching an infusion tube by opening an access cover of the infusion pump illustrated in FIGS. 1 and 2.

In FIG. 3, the access cover 5 of the infusion pump 1 illustrated in FIGS. 1 and 2 is opened and the tube attachment section 50 for attaching the infusion tube 200 and the liquid feed driving unit 60 are illustrated.

As illustrated in FIG. 3, the tube attachment section 50 and the liquid feed driving unit 60 are disposed at a main body lower portion 1B (lower portion 2B of the main body cover 2) of the infusion pump 1, and the tube attachment section 50 and liquid feed driving unit 60 are arranged along the X-direction below the display unit 3 and the operation panel 4. The tube attachment section 50 and the liquid feed driving unit 60 can be covered by the access cover 5 when the access cover 5 is closed in the CR-direction, centering the rotary shaft 5A, as illustrated in FIG. 2.

The medical staff can attach the infusion tube 200 to the tube attachment section 50 while confirming the information on the display unit 3 at the upper portion 2A of the main body cover 2, and can close the access cover 5. Further, the medical staff can operate the operating buttons on the operation panel 4 while confirming the information on the display unit 3 at the upper portion 2A of the main body cover 2. This can improve operability of the infusion pump 1 at a medical site.

As illustrated in FIG. 3, the tube attachment section 50 includes a bubble detection unit 51, an upstream block sensor 52, a downstream block sensor 53, a tube clamp unit 270, a first infusion tube guide unit 54 on the right side, and a second infusion tube guide unit 55 on the left side.

As illustrated in FIG. 3, an infusion tube setting direction display unit 150 is provided at the vicinity of the tube attachment section 50 in order to clearly indicate the correct feeding direction T at the time of setting the infusion tube 200. The infusion tube setting direction display unit 150 is, for example, formed of a plurality of arrows 151. The infusion tube setting direction display unit 150 may be, for example, directly printed at a lower portion of the tube attachment section 50, or may be printed on a sticker-like member so as to be pasted on the lower portion of the tube attachment section 50. The infusion tube setting direction display unit 150 is disposed in order to clearly indicate the correct direction of feeding direction (feeding direction T) of the medicinal solution 171 by the infusion tube 200 set on the inner side of the access cover 5.

With this configuration, the feeding direction T of the medicinal solution by the infusion tube 200 can be clearly indicated when the medical staff opens the access cover 5 of FIG. 3 in the CS-direction and exposes the tube attachment section 50 to attach the infusion tube 200 to the tube attachment section 50. Therefore, the medical staff can prevent the infusion tube 200 from being incorrectly attached in an opposite direction while visual confirming.

Next, an exemplary structure of the access cover 5 illustrated in FIG. 3 will be described.

As illustrated in FIG. 3, the access cover 5 is the plate-like member made of a thin molded resin member for reducing the weight of the infusion pump 1. This can reduce the weight of the access cover 5 and can also simplify the structure. The access cover 5 can be opened and closed in the CS-direction and the CR-direction, centering the rotary shaft 5A such that the access cover 5 can cover the tube attachment section 50 and the liquid feed driving unit 60. More specifically, the access cover 5 is supported with two hinges 2H, 2H with respect to the lower portion 2B of the main body 2. The two hinges 2H, 2H are disposed corresponding to a first hook member 5D and a second hook member 5E respectively.

As illustrated in FIG. 3, an open/close operation lever 260 is disposed at an upper right portion on the front surface side of the access cover 5. An infusion tube pressing member 500, the first hook member 5D, and the second hook member 5E are disposed on an inner surface side of the access cover 5. The infusion tube pressing member 500 is disposed along the X-direction as a rectangular and planner shaped projecting portion, and the infusion tube pressing member 500 is positioned facing the liquid feed driving unit 60. The infusion tube pressing member 500 has a flat face along the liquid feed driving unit 60 in the X-direction, and the infusion tube pressing member 500 is configured to press and sandwich a part of the infusion tube 200 in a space with the liquid feed driving unit 60 by closing the access cover 5 in the CR-direction.

The medical staff can set the infusion tube 200 at the lower portion 2B of the main body 2 of the infusion pump 1 in the horizontal direction while confirming indicated contents displayed on the display unit 3, and the infusion tube 200 can be covered by closing the access cover 5 in the CR-direction as illustrated in FIGS. 1 and 2 after the infusion tube 200 is set to the tube attachment section 50 and the liquid feed driving unit 60.

As illustrated in FIG. 3, the respective first hook member 5D and second hook member 5E are mechanically hooked at fixing portions 1D, 1E on the main body lower portion 1B side in parallel, thereby the access cover 5 keeps the tube attachment section 50 and the liquid feed driving unit 60 at the main body lower portion 1B in a closed state as illustrated in FIG. 2. The first hook member 5D, second hook member 5E, and fixing portions 1D, 1E on the main body lower portion 1B side constitute a double hook structure 300 of the access cover 5.

A tube clamp unit 270 illustrated in FIG. 3 clamps and blocks a middle portion of the infusion tube 200 by closing the access cover 5. The tube clamp unit 270 is disposed in the vicinity of the left-side fixing portion 1E at a position corresponding to the left-side second hook member 5E. When the medical staff horizontally sets the infusion tube 200 in the X-direction and the medical staff closes the access cover 5 in the CR-direction, the tube clamp unit 270 can block a part of the middle part of the infusion tube 200.

As illustrated in FIG. 3, the first infusion tube guide unit 54 is disposed on the right-side portion of the main body lower portion 1B and the second infusion tube guide unit 55 is disposed on the left-side portion of the main body lower portion 1B when the person faces the main body. The infusion tube 200 is held in the horizontal direction along the X-direction by fitting an upstream side 200A of the infusion tube 200 in first infusion tube guide unit 54 and fitting a downstream side 200B of the infusion tube 200 in the second infusion tube guide unit 55. The infusion tube 200 thus horizontally held is fixed by being fitted in the feeding direction T along the bubble detection unit 51, upstream block sensor 52, liquid feed driving unit 60, downstream block sensor 53, and tube clamp unit 270.

As illustrated in FIG. 3, the first infusion tube guide unit 54 includes two protrusions 54B, 54C and a slanted guide portion 54T. The two protrusions 54B, 54C are formed at the main body lower portion 1B in order to detachably sandwich and hold the upstream side 200A of the infusion tube 200 at the time of setting the infusion tube 200 in the horizontal direction. The slanted guide portion 54T is formed in an oblique upper-right direction from the two protrusions 54B, 54C and guides the upstream side 200A of the infusion tube 200 in an oblique upper direction.

By providing the slanted guide portion 54T, the medical staff not only can visually confirm that the upstream side 200A of the infusion tube 200 is set on the slanted guide portion 54T side but also can hold the upstream side 200A of the infusion tube 200 so as not to be rapidly curved. Moreover, since the slanted guide portion 54T is not covered with the access cover 5 and exposed, the medical staff can confirm that the upstream side 200A of the infusion tube 200 is to be set on the slanted guide portion 54T side by directly and visually checking the slanted guide portion 54T.

As illustrated in FIG. 3, the second infusion tube guide unit 55 is a groove portion formed at a side surface portion 1S of the main body lower portion 1B in order to detachably sandwich and hold a part of the downstream side 200B of the infusion tube 200. The first infusion tube guide unit 54 and the second infusion tube guide unit 55 can surely attach the infusion tube 200 to the inside of the tube attachment section 50 without damaging the infusion tube when sandwiching the infusion tube between the access cover 5 and the tube attachment section 50. As illustrated in FIGS. 1 and 2, a right side surface portion 5K of the access cover 5 is formed slanted in an oblique upper-left direction. This prevents the access cover 5 from covering the two protrusions 54B, 54C of the first infusion tube guide unit 54 and the slanted guide portion 54T even when the access cover 5 is in the closed state.

The bubble detection unit 51 illustrated in FIG. 3 is a sensor to detect a bubble (air) generated inside the infusion tube 200. For example, the bubble detection unit 51 is an ultrasonic sensor configured to monitor, from the outside of the infusion tube 200 of flexible polyvinyl chloride or the like, the bubble contained inside the medicinal solution flowing inside the infusion tube 200. Since transmissivity of ultrasonic in the medicinal solution differs from the transmissivity of the ultrasonic in the bubble, the ultrasonic receiving unit detects a difference of the transmissivity and monitors existence of the bubble by applying the ultrasonic generated from the ultrasonic transmitting unit to the medicinal solution flowing inside the infusion tube 200. The bubble detection unit 51 includes a pushing member 320 and a receiving member 330. The ultrasonic transmitting unit is embedded in the pushing member 320 disposed on the inner side of the access cover 5, the detail of which will be described later. The ultrasonic receiving unit is embedded in the receiving member 330 disposed on the lower portion 2B side of the main body 2.

The upstream block sensor 52 illustrated in FIG. 3 is a sensor that detects whether the inside of the infusion tube 200 is blocked at the upstream side 200A of the infusion tube 200, and the downstream block sensor 53 is a sensor that detects whether the inside of the infusion tube 200 is blocked at the downstream side 200B of the infusion tube 200. The upstream block sensor 52 and the downstream block sensor 53 have the same structure. The cases where the infusion tube 200 is blocked are when the medicinal solution has high viscosity, the medicinal solution has high concentration, or the like, for example.

As illustrated in FIG. 3, pressing members 452, 453 are respectively disposed on the inner surface side of the access cover 5 at positions corresponding to the upstream block sensor 52 and downstream block sensor 53. When the medical staff closes the access cover 5 as illustrated in FIG. 2 after setting the infusion tube 200 to the tube attachment section 50 as illustrated in FIG. 3, the pressing member 452 and the pressing member 453 on the access cover 5 side can respectively press a part of the infusion tube 200 against the upstream block sensor 52 and downstream block sensor 53 side. Therefore, when the access cover 5 is closed, the upstream block sensor 52 and the downstream block sensor 53 can detect a blocked state in the infusion tube 200 even in the case where any size of the infusion tube 200 out of a plurality of kinds of infusion tubes 200 having different diameters is attached to the infusion pump 1.

Figure 4:
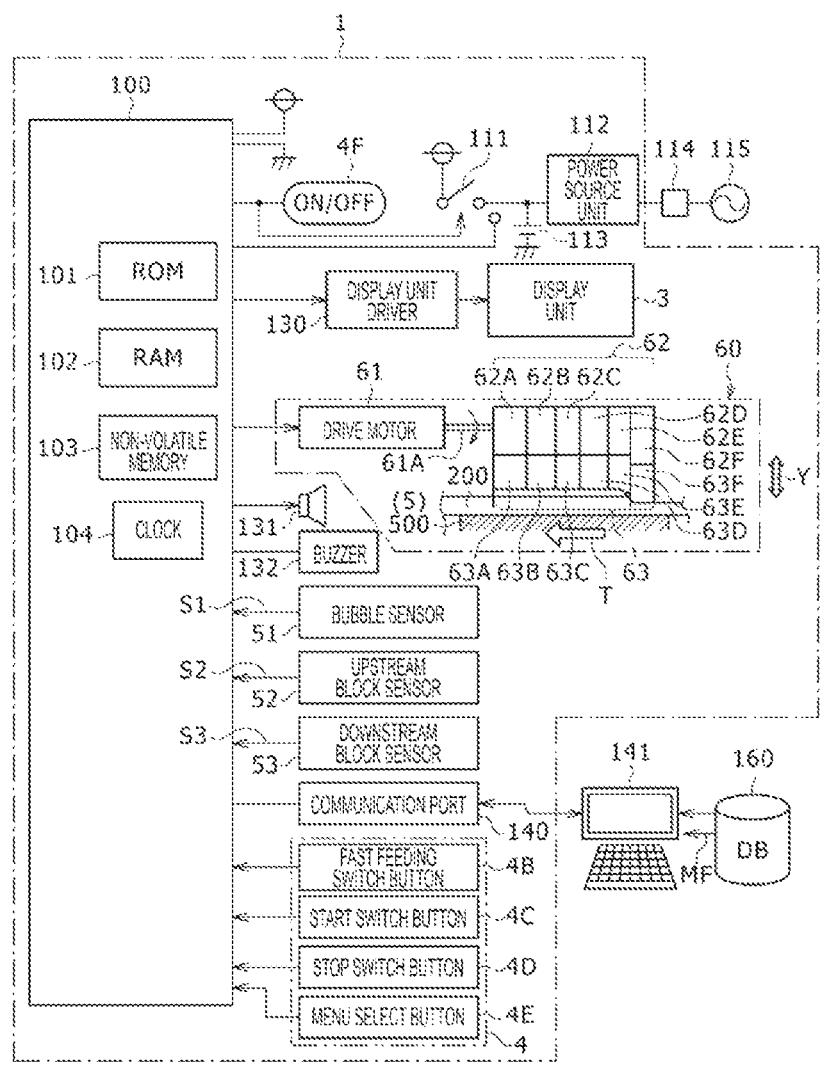
FIG. 4 is a diagram illustrating an electrical configuration of the infusion pump of FIG. 1.

FIG. 4 is a diagram illustrating an electrical configuration of the infusion pump 1.

As illustrated in FIG. 4, the liquid feed driving unit 60 includes a drive motor 61, a cam structure 62 rotationally driven by the drive motor 61 and including a plurality of cams, and a finger structure 63 including the plurality of fingers moved by the respective cams of the cam structure 62.

The cam structure 62 includes the plurality of cams, for example, six cams 62A to 62F, and the finger structure 63 includes six fingers 63A to 63F corresponding to the six cams 62A to 62F. The six cams 62A to 62F are arranged at phases different one another, and the cam structure 62 is connected to an output shaft 61A of the drive motor 61.

When the output shaft 61A of the drive motor 61 is rotated by a command of a control unit 100 illustrated in FIG. 4, the six fingers 63A to 63F are moved forward and backward in the Y-direction in a predetermined order by an amount of a predetermined stroke, thereby pressing the infusion tube 200 against the infusion tube pressing member 500 of the access cover 5 in the feeding direction T. Therefore, the medicinal solution inside the infusion tube 200 can be fed in the feeding direction T. More specifically, since the plurality of fingers 63A to 63F are respectively driven, the plurality of fingers 63A to 63F sequentially press the outer peripheral surface of the infusion tube 200 in the feeding direction T and feed the medicinal solution inside the infusion tube 200. The fingers 63A to 63F are sequentially moved forward and backward by controlling peristaltic motion of the plurality of fingers 63A to 63F, and a block point of the infusion tube 200 is moved in the feeding direction T like advancement of a wave. With this motion, the infusion tube 200 is stroked to transfer the medicinal solution As illustrated in FIG. 4, the infusion pump 1 includes the control unit (computer) 100 that controls entire operation. The control unit 100 is, for example, a one-chip microcomputer and includes a ROM (read-only memory) 101, a RAM (Random Access Memory) 102, a non-volatile memory 103, and a clock 104. The clock 104 can correct current time by a predetermined operation, acquire the current time, measure an elapsed period of a predetermined feeding operation, measure reference time for feeding rate control, and so on.

The control unit 100 illustrated in FIG. 4 is connected to the power switch button 4F and a switch 111. The switch 111 supplies power to the control unit 100 from any one of a power supply converter 112 and a rechargeable battery 113 such as a lithium ion battery by switching between the power supply converter 112 and the rechargeable battery 113. The power supply converter 112 is connected to a commercial AC power supply 115 via an electric point 114.

A display unit driver 130 in FIG. 4 drives the display unit 3 by a command of the control unit 100 and displays the contents of information exemplified in FIG. 2 and a warning message. A speaker 131 can notify the medical staff of various kinds of warning information by voice in accordance with a command from the control unit 100. A buzzer 132 can notify the medical staff of the various kinds of warnings by sound in accordance with a command from the control unit 100. In the case where the infusion tube 200 is incorrectly set in N-direction (opposite direction), the speaker 131 is one of the exemplary warning means that issues the warning to the medical staff by voice. In the case where the infusion tube 200 is incorrectly set in N-direction (opposite direction), the buzzer 132 is one of the exemplary warning means that issues the warning to the medical staff by sound.

In FIG. 4, a bubble detection signal S1 from the bubble detection unit 51, an upstream block signal S2 from the upstream block sensor 52 indicating that the upstream side of the infusion tube 200 is blocked, and a downstream block signal S3 from the downstream block sensor 53 indicating that the downstream side of the infusion tube 200 is blocked are supplied to the control unit 100. The upstream block sensor 52 and the downstream block sensor 53 can detect a state that the medicinal solution cannot be fed due to the fact that inner pressure of an infusion circuit exceeds setting pressure inside the infusion pump 1. The inner pressure of the infusion circuit exceeding the setting pressure inside the infusion pump 1 is caused in the cases where the intravenous cannula for infusion or the infusion tube 200 are blocked, the infusion tube 200 is squeezed or bent, the medicinal solution having high viscosity is used, and the like.

In FIG. 4, the control unit 100 can bidirectionally communicate with, for example, a computer 141 such as a desktop computer via a communication port 140. The computer 141 is connected to the medicinal solution database (DB) 160, and medicinal solution information MF stored in the medicinal solution database 160 can be acquired by the control unit 100 via the computer 141 and stored in the non-volatile memory 103 of the control unit 100. The control unit 100 displays the medicinal solution information MF or the like on the display unit 3 illustrated in FIG. 2, for example, based on the stored medicinal solution information MF.

Figure 5:
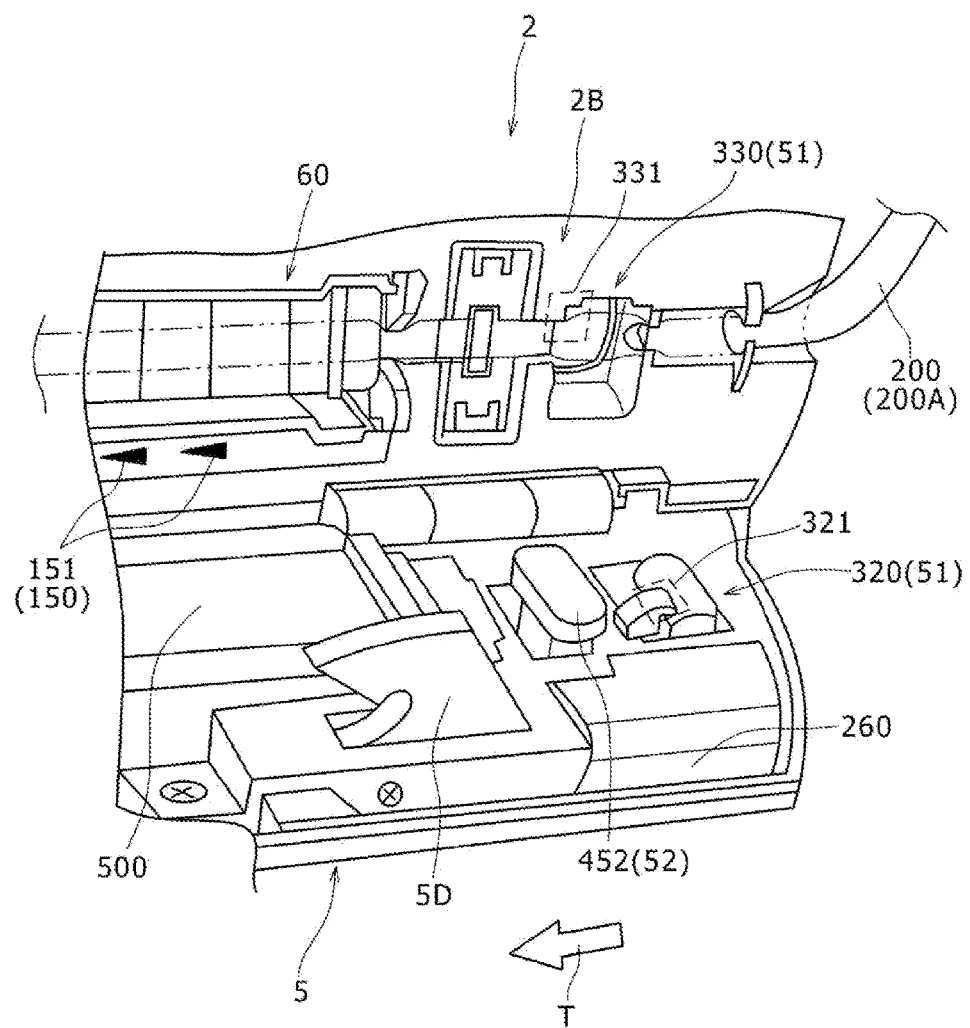
FIG. 5 is a perspective view illustrating an enlarged view of a lower portion of a main body and the access cover of the infusion pump illustrated in FIG. 3.

FIG. 5 is a perspective view illustrating an enlarged view of the lower portion 2B of the main body 2 and the access cover 5 of the infusion pump 1 illustrated in FIG. 3.

The bubble detection unit 51 illustrated in FIG. 5, also referred to as a bubble sensor, detects the existence of a bubble (air) inside the infusion tube 200. The bubble detection unit 51 is an ultrasonic sensor to monitor the bubble contained inside the medicinal solution flowing inside the infusion tube 200. An ultrasonic transmitting unit 321 of the bubble detection unit 51 is disposed inside the pushing member 320. On the other hand, an ultrasonic receiving unit 331 of the bubble detection unit 51 is disposed inside the receiving member 330. Note that the ultrasonic transmitting unit 321 may be disposed inside the receiving member 330 and the ultrasonic receiving unit 331 may be disposed inside the pushing member 320. Further, a magnetic (electromagnetic) shield (not illustrated) is provided at the ultrasonic transmitting unit 321 and the ultrasonic receiving unit 331.

As illustrated in FIGS. 1 and 2, when the access cover 5 is closed, the pushing member 320 in FIG. 5 pushes the infusion tube 200 against the receiving member 330 so as to squeeze the infusion tube 200 by a predetermined amount. The pushing member 320 and the receiving member 330 are both plastic molded products having electrical insulation properties.

As illustrated in FIG. 5, the pushing member 320 is disposed on the inner side of the access cover 5 and, the receiving member 330 is disposed at the lower portion 2B of the main body 2. Since transmissivity of the ultrasonic in the medicinal solution differs from the transmissivity of the ultrasonic in the bubble (or medicinal solution containing the bubble), the ultrasonic receiving unit 331 of the receiving member 330 detects a difference of transmissivity as an output potential difference from a threshold value, for example, and monitors existence of the bubble by applying the ultrasonic generated from the ultrasonic transmitting unit 321 of the pushing member 320 to the medicinal solution flowing inside the infusion tube 200.

Figure 6A:
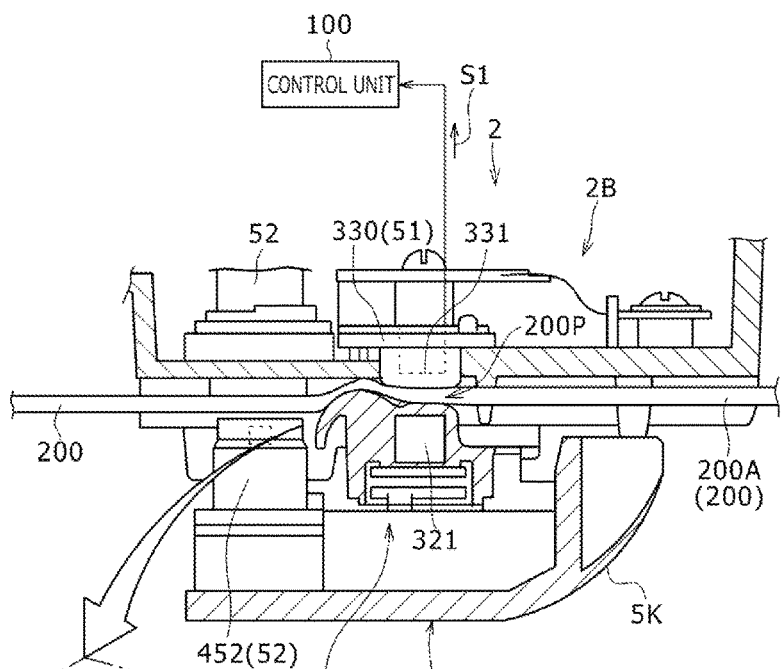
FIG. 6(A) is a diagram illustrating a cross-section taken along line E-E when the access cover covers the lower portion of the main body as illustrated in FIGS. 1 and 2.
Figure 6B:
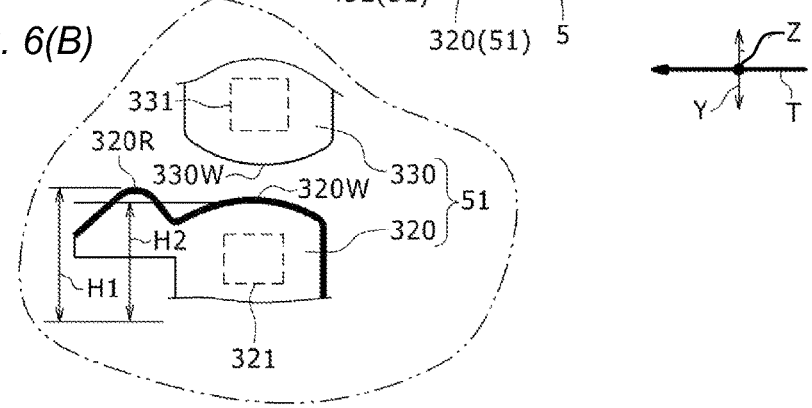
FIG. 6(B) is an enlarged view of a portion of FIG. 6(A).

FIG. 6 is a cross-sectional view taken along line E-E when the access cover 5 covers the lower portion 2 of the main body 2 as illustrated in FIGS. 1 and 2. FIG. 6(B) is an enlarged view of a portion of FIG. 6(A)

In FIG. 6(A), the vicinity of the side surface portion 5K on the right side of the access cover 5 and a part of the lower portion 2B of the main body 2 are illustrated, and the pushing member 320 of the bubble detection unit 51 disposed on the access cover 5 and the receiving member 330 of the bubble detection unit 51 face each other.

The pushing member 320 which is a first member of the bubble detection unit 51 includes a projecting curved surface portion 320W, and the receiving member 330 which is a second member of the bubble detection unit 51 includes a projecting curved surface portion 330W. The curved surface portion 320W and the curved surface portion 330W are disposed at mutually facing positions. A middle portion 200P of the infusion tube 200 is pushed between the projecting curved surface portion 320W of the pushing member 320 and projecting curved surface portion 330W of the receiving member 330 by a predetermined amount, and the middle portion 200P is elastically deformed. The ultrasonic transmitting unit 321 of the pushing member 320 and the ultrasonic receiving unit 331 of the receiving member 330 face each other.

Figure 7:
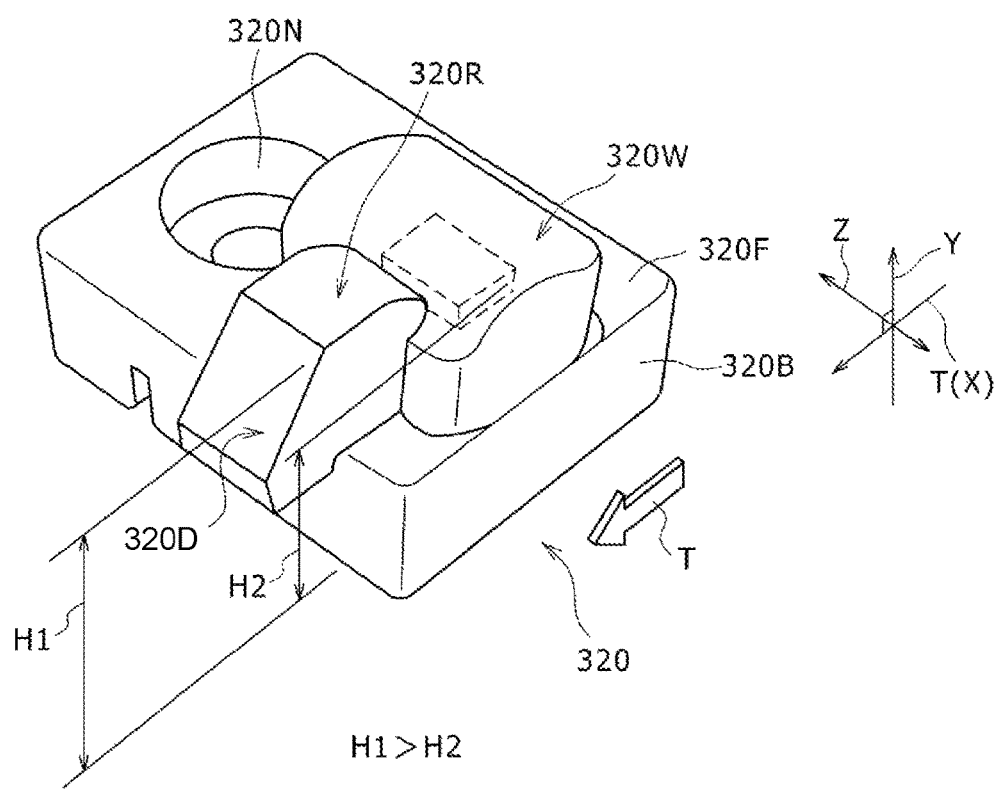
FIG. 7 is a perspective view illustrating a form of a pushing member.

Now, a preferred shape of the pushing member 320 will be described with reference to FIGS. 6(A), 6(B), and 7. FIG. 7 is a perspective view illustrating the form of the pushing member 320.

The pushing member 320 illustrated in FIG. 7 includes a base portion 320B, the projecting curved surface portion 320W, and a projecting portion 320D. The base portion 320B is a cuboid shaped member, and includes a screw hole 320N for passing a screw in order to fix the pushing member 320. The projecting curved surface portion 320W is formed on one surface 320F of the base portion 320B in a projecting manner in the Y-direction. The projecting portion 320D is located immediately next to the projecting curved surface portion 320W, and formed in a projecting manner in the Y-direction on the downstream side of the feeding direction T.

The projecting portion 320D includes a pressing portion 320R to press the middle portion 200P of the infusion tube 200. A height H1 of the pressing portion 320R projecting from a bottom portion of the base portion 320B in the Y-direction is set higher compared to a height H2 of the projecting curved surface portion 320W projecting from a bottom portion of the base portion 320B in the Y-direction.

Next, operation at the time of using the above-described infusion pump 1 will be described.

As illustrated in FIG. 3, the medical staff can look at the infusion tube setting direction display unit 150 and visually confirm the setting direction of the infusion tube 200 at the time of opening the access cover 5 and setting the infusion tube 200 to the tube attachment section 50. Also, the medical staff opens the access cover 5, sets the upstream side 200A of the infusion tube 200 to the first infusion tube guide unit 54 side on the right side portion of the main body lower portion 1B, and sets the downstream side 200B of the infusion tube 200 to the second infusion tube guide unit 55 side on the left side of the main body lower portion 1B when a person faces the main body. In this manner, the medical staff can correctly set the infusion tube 200 in the feeding direction T with respect to the infusion pump 1. The medical staff can set the infusion tube 200 illustrated in FIG. 4 in the feeding direction T along the first infusion tube guide unit 54, bubble detection unit 51, upstream block sensor 52, liquid feed driving unit 60, downstream block sensor 53, tube clamp unit 270, and second infusion tube guide unit 55.

After that, by closing the access cover 5 as illustrated in FIGS. 1 and 2, the access cover 5 covers the bubble detection unit 51, upstream block sensor 52, downstream block sensor 53, liquid feed driving unit 60, and tube clamp unit 270. In this state, the liquid feed driving unit 60 is driven, thereby feeding the medicinal solution through the infusion tube 200 in the feeding direction T. Further, the medical staff can operate the operating buttons on the operation panel 4 while confirming the information on the display unit 3 at the upper portion 2A of the main body cover 2.

In the case where the infusion pump 1 feeds the medicinal solution to the patient by using the infusion tube 200 as described above, the bubble detection unit 51 illustrated in FIG. 4 detects whether a bubble is mixed inside the medicinal solution inside the infusion tube 200. When the bubble detection unit 51 detects existence of a bubble inside the infusion tube 200, the ultrasonic receiving unit 331 of the bubble detection unit 51 illustrated in FIG. 6 is configured to transmit the bubble detection signal S1 to the control unit 100.

Figure 8A:
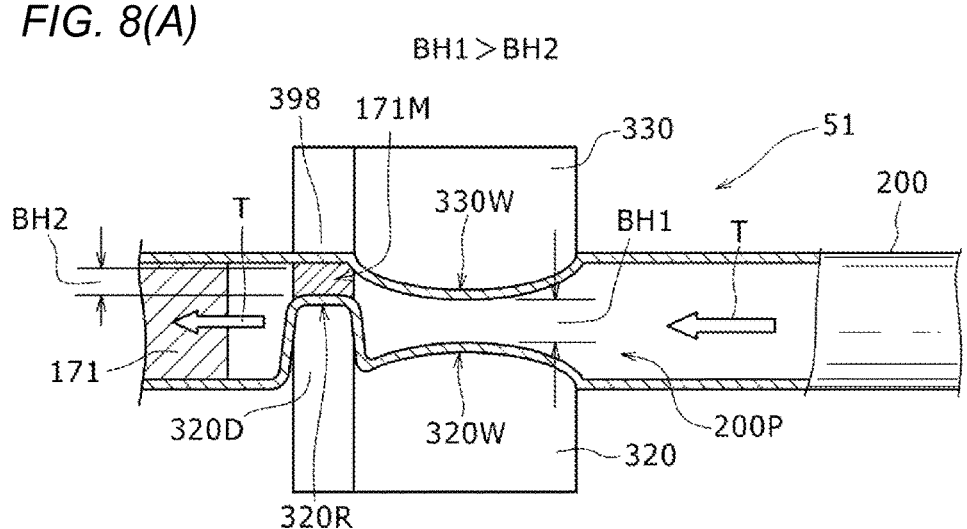
FIG. 8(A) is a diagram illustrating behavior of a medicinal solution inside the infusion tube in the case of using the bubble sensor illustrated in FIG. 6 according to the embodiment of the present invention.
Figure 8B:
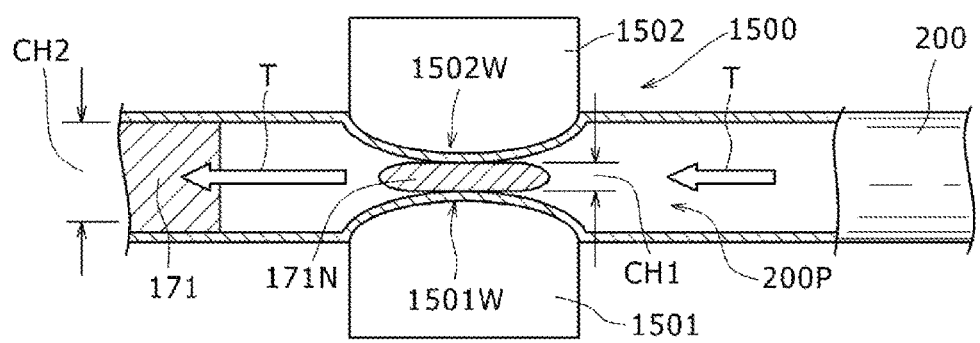
FIG. 8(B) is a diagram illustrating the behavior of the medicinal solution inside the infusion tube in the case of using a bubble sensor in the related art as a comparative example.

FIG. 8(A) is a diagram illustrating behavior of the medicinal solution 171 inside the infusion tube 200 in the case of using the bubble detection unit 51 illustrated in FIG. 6 according to the embodiment of the present invention. FIG. 8(B) is a diagram illustrating the behavior of the medicinal solution 171 inside the infusion tube 200 in the case of using a bubble sensor 1500 in a related art.

In the bubble detection unit 51 according to the embodiment of the present invention illustrated in FIG. 8(A), a space BH1 represents clearance of the flow path at the middle portion 200P of the infusion tube 200 formed between the projecting curved surface portion 320W of the pushing member 320 and the projecting curved surface portion 330W of the receiving member 330.

Another space BH2 represents clearance of the flow path at the middle portion 200P of the infusion tube 200 formed between the pressing portion 320R of the projecting portion 320D and a facing wall portion 398 facing the pressing portion 320R.

The space BH2 is located on the more downstream side of the feeding direction T compared to the space BH1. The space BH2 is set smaller than the space BH1. Therefore, the middle portion 200P of the infusion tube 200 has the narrower flow path (flow path cross-section area) at the space BH2 compared to that at the space BH1.

Thus, since the space BH2 smaller than the space BH1 of the bubble detection unit 51 is provided on the downstream side of the feeding direction T of the bubble detection unit 51 as illustrated in FIG. 8(A), the flow path at the middle portion 200P of the infusion tube 200 on the downstream side of the bubble detection unit 51 is narrower than the flow path at the middle portion 200P of the infusion tube 200 sandwiched between the members of the bubble detection unit 51. Therefore, the medicinal solution 171 can stagnate in the flow path at the middle portion 200P of the infusion tube 200 on the downstream side of the bubble detection unit 51 instead of stagnating in the flow path at the middle portion 200P of the infusion tube 200 between the members of the bubble detection unit 51. Such a stagnation phenomenon of the medicinal solution 171 is the phenomenon in which the medicinal solution partly stagnates at the narrow portion of the flow path of the infusion tube 200 as a, what is called, liquid stagnant portion 171M.

The stagnation phenomenon of the medicinal solution 171 in the liquid stagnant portion 171M is positively generated between the pressing portion 320R of the projecting portion 320D on the downstream side of the bubble detection unit 51 and the facing wall portion 398 facing the pressing portion 320R instead of being generated between the projecting curved surface portion 320W of the pushing member 320 and the projecting curved surface portion 330W of the receiving member 330 of the bubble detection unit 51. In other words, the portion between the pressing portion 320R of the projecting portion 320D on the downstream side of the bubble detection unit 51 and the facing wall portion 398 facing the pressing portion 320R is a place where a flow rate of the medicinal solution 171 changes and the surface tension of the medicinal solution 171 tends to break.

Therefore, the bubble detection unit 51 is prevented from erroneously detecting the liquid stagnant portion 171M because the so-called liquid stagnant portion 171M of the medicinal solution 171 is not left out between the pushing member 320 and the receiving member 330 of the bubble detection unit 51. As a result, the liquid stagnant portion 171M, namely, a part of the medicinal solution 171 is not left over between the pushing member 320 and the receiving member 330 of the bubble detection unit 51. Therefore, the ultrasonic from the ultrasonic transmitting unit 321 of the bubble detection unit 51 is prevented from being transmitted through the liquid stagnant portion 171M and received by the ultrasonic receiving unit 331. Due to this, the bubble detection unit 51 does not determine that the medicinal solution exists inside the infusion tube 200, and therefore, existence of the bubble can be detected without interruption of the liquid stagnant portion 171M when the bubble exists in the infusion tube 200. In other words, the bubble detection unit 51 can prevent error detection of existence of the medicinal solution 171 caused by the liquid stagnant portion 171M of medicinal solution 171.

As described above, according to the embodiment of the present invention, the liquid stagnant portion 171M of the medicinal solution 171 can be generated on the downstream side of the bubble detection unit 51 because the flow path of the infusion tube 200 on the downstream side of the bubble detection unit 51 is formed narrower than the flow path of the infusion tube 200 formed by the bubble detection unit 51.

On the other hand, according to the bubble sensor 1500 in the comparative example illustrated in FIG. 8(B), there is no pressing member to press the middle portion 200P that is provided on the downstream side of the middle portion 200P of the infusion tube 200. Therefore, a space CH1 between a projecting curved surface portion 1501W of a pushing member 1501 and a projecting curved surface portion 1502W of a receiving member 1502 of the bubble sensor 1500 is smaller compared to an inner diameter CH2 of the middle portion 200P of the infusion tube 200 on the downstream side of the feeding direction T.

With this configuration, the bubble sensor 1500 detects the liquid stagnant portion 171N because the liquid stagnant portion 171N of the medicinal solution 171 is left out due to the fact that the flow rate changes between the pushing member 1501 and the receiving member 1502 of the bubble sensor 1500. Therefore, the bubble sensor 1500 determines that the medicinal solution 171 is flowing inside the infusion tube 200.

FIGS. 9(A) and 9(B) are a diagrams illustrating a state in which the flow path of the infusion tube 200 is narrowed by the infusion tube 200 being pressed by the bubble sensor 1500 in the related art as illustrated in FIG. 8(B), but the liquid stagnant portion of the medicinal solution 171 is not generated and the medicinal solution normally flows in the feeding direction T. In contrast, FIGS. 9(C) and 9(D) are a diagrams illustrating a state in which the flow path of the infusion tube 200 is narrowed by the infusion tube 200 being pressed by the bubble sensor 1500 in the related art as illustrated in FIG. 8(B), and the liquid stagnant portion 171N of the medicinal solution 171 is generated and clearance (bubble) AR is formed.

In the case of FIGS. 9(C) and 9(D) where the liquid stagnant portion 171N is generated, the clearance AR is formed at an upper portion of the liquid stagnant portion 171N, and the air passes through the clearance AR, but the liquid stagnant portion 171N stagnates inside bubble sensor 1500. When a boundary between the liquid stagnant portion 171N and the air passes the portion where the flow path is narrowed by the bubble sensor 1500, a part of the medicinal solution is caught at the inner surface of the infusion tube 200 due to the influences of the surface tension of the medicinal solution and gravity as well as a suction speed and suction timing of the medicinal solution. As a result, the medicinal solution may remain as the liquid stagnant portion 171N (part of the medicinal solution). When the liquid stagnant portion 171N occupies a large part of the flow path of the infusion tube 200, ultrasonic from the ultrasonic transmitting unit of the bubble sensor is transmitted to the liquid stagnant portion 171N and received by the ultrasonic receiving unit. Therefore, the control unit erroneously determines that the medicinal solution is flowing although the clearance (bubble) AR exists inside the infusion tube 200.

As described above, the infusion pump 1 according to the embodiment of the present invention includes; the main body 2; the tube attachment section 50 disposed inside the main body 2, where the infusion tube 200 configured to feed the medicinal solution 171 to the patient side is attached in the lateral direction; the liquid feed driving unit 60 disposed inside the main body 2 and configured to feed the medicinal solution in the lateral direction through the inside of the infusion tube 200 by pressing the infusion tube 200 in a state that the infusion tube 200 is attached to the tube attachment section 50; the access cover 5 mounted on the main body 2 and configured to cover the infusion tube 200 attached to the tube attachment section 50 by being closed; and the bubble detection unit 51 configured to detect the bubble inside the infusion tube 200 by receiving the ultrasonic generated with respect to the infusion tube 200 attached to the tube attachment section 50.

The bubble detection unit 51 includes the pushing member 320 as the first member disposed on the access cover 5 and having the ultrasonic transmitting unit 321 and the receiving member 330 as the second member disposed on the main body 2 and having the ultrasonic receiving unit 31 configured to receive the ultrasonic from the ultrasonic transmitting unit 321. Further, when the access cover 5 is in the closed state, the second space BH2 to narrow the flow path of the infusion tube 200 on the more downstream side than the bubble detection unit 51 in the feeding direction T of feeding the medicinal solution 171 of the infusion tube 200 is set smaller compared to the first space BH1 to narrow the flow path of the infusion tube 200 between the first member and the second member.

With this configuration, the stagnation phenomenon at the liquid stagnant portion of the medicinal solution can be generated on the downstream side of the bubble sensor instead of being generated between the members of the bubble sensor because the second space BH2 to narrow the flow path of the infusion tube 200 on the more downstream side than the bubble detection unit 51 is set smaller compared to the first space BH1 to narrow the flow path of the infusion tube 200 between the first member and the second member. This is because the surface tension of the medicinal solution tends to break at the portion where the flow rate of the medicinal solution rapidly changes. Therefore, the bubble sensor is prevented from erroneously detecting the liquid stagnant portion because the so-called liquid stagnant portion of the medicinal solution is not left out between the first member and the second members of the bubble sensor. As a result, the bubble sensor can be prevented from erroneously detecting existence of the bubble by avoiding a part of the medicinal solution remaining inside the portion where the flow path of the infusion tube is narrowed by the bubble sensor.

The first member includes the base portion 320B, the projecting curved surface portion 320W formed in a projecting manner from the base portion 320B, and the projecting portion 320D formed in a projecting manner on the more downstream side than the projecting curved surface portion 320W in order to set the second space BH2. The second member includes the projecting curved surface portion 330W facing the projecting curved surface portion 320W of the first member and set the first space.

Therefore, since the projecting portion 320D to set the second space BH2 is integrally formed with the first member, the number of components can be more reduced compared to a case where the projecting portion 320D is provided as a separate member from the first member.

The projecting height H1 from the base portion 320B of the projecting portion 320D is set higher compared to the projecting height H2 from the base portion 320B of the projecting curved surface portion 320W in the first member. Therefore, the second space BH2 formed by the projecting portion 320D can be set smaller compared to the first space BH1 of the bubble detection unit 51 just by disposing the first member.

The display unit 3 and operation panel 4 are disposed at the upper portion 2A of the main body 2, and the tube attachment section 50, liquid feed driving unit 60, and access cover 5 are disposed at the lower portion 2B of the main body 2. Therefore, the medical staff can attach the infusion tube 200 to the tube attachment section 50 while confirming the information on the display unit 3 at the upper portion 2A of the main body 2, and close the access cover 5. Further, the medical staff can operate the operation buttons at the operation panel 4 while confirming the information on the display unit 3 at the upper portion 2A of the main body 2.

The present invention is not limited the above-described embodiment and various kinds of corrections and changes can be made to the present invention, and also modifications can be made within the range recited in the scope of claims.

The bubble detection unit 51 exemplified in the drawings may be modified. For example, the projecting portion 320D is provided only on the pushing member 320 side, but not limited thereto. The projecting portion may be also provided on the receiving member 330 side such that the projecting portion 320D on the pushing member 320 side and the projecting portion on the receiving member 330 side narrow the flow path of the infusion tube on the downstream side of the bubble sensor.

According to the examples illustrated in FIGS. 1 and 2, the infusion tube 200 is set completely horizontally in the feeding direction T by the tube attachment section 50. However, the infusion tube 200 is not limited to that setting. The tube attachment section 50 may adopt a structure in which the infusion tube 200 is set in the horizontal direction, but being sloped downward at a predetermined angle from the upstream side 200A to the downstream side 200B, for example.

What is claimed is:

1. An infusion pump comprising:
a main body;
a tube attachment section disposed inside the main body, in which an infusion tube configured to feed a medicinal solution to a patient side of the infusion pump is attachable;
a liquid feed driving unit disposed inside the main body and configured to feed the medicinal solution inside the infusion tube by pressing the infusion tube when the infusion tube is attached to the tube attachment section;
an access cover mounted on the main body and configured to cover the infusion tube when the infusion tube is attached to the tube attachment section when closed; and
a bubble detection unit configured to detect a bubble inside the infusion tube when the infusion tube is attached to the tube attachment section,
wherein the bubble detection unit includes a first member disposed at the access cover and a second member disposed at the main body,
wherein the infusion pump is configured such that, when the infusion tube is attached to the tube attachment section, closing the access cover causes the first member and the second member to squeeze and deform the infusion tube and thereby form a first space of the infusion tube located between the first member and the second member of the bubble detection unit, and a second space of the infusion tube located downstream of the first space, the second space being smaller than the first space, and the second space being immediately adjacent to the first space.

2. The infusion pump according to claim 1,
wherein the first member includes a base portion, a first projecting curved surface portion formed in a projecting manner from the base portion, and a projecting portion formed in a projecting manner from the base portion located downstream of the first projecting curved surface portion,
wherein the second member includes a second projecting curved surface portion facing the first projecting curved surface portion of the first member,
wherein the second projecting curved surface portion and the first projecting curved surface portion are configured to set the first space, and
wherein the projecting portion is configured to set the second space.

3. The infusion pump according to claim 2, wherein a projecting height of the projecting portion from the base portion is greater than a projecting height of the first projecting curved surface portion from the base portion.

4. The infusion pump according to claim 3, wherein one of the first member and the second member includes an ultrasonic transmitting unit and the other of the first member and the second member includes an ultrasonic receiving unit.

5. The infusion pump according to claim 4, wherein an electromagnetic shield is provided at the ultrasonic transmitting unit and the ultrasonic receiving unit.

6. The infusion pump according to claim 4, wherein the ultrasonic receiving unit is configured to transmit a bubble detection signal to a control unit.

7. The infusion pump according to claim 1,
wherein the first member includes a base portion and a first projecting curved surface portion formed in a projecting manner from the base portion,
wherein the second member includes a second projecting curved surface portion facing the first projecting curved surface portion of the first member,
wherein the infusion pump includes a projecting portion formed in a projecting manner located downstream of the first projecting curved surface portion,
wherein the second projecting curved surface portion and the first projecting curved surface portion are configured to set the first space, and
wherein the projecting portion is configured to set the second space.

8. The infusion pump according to claim 7, wherein a projecting height of the projecting portion is greater than a projecting height of the first projecting curved surface portion.

9. The infusion pump according to claim 8, wherein one of the first member and the second member includes an ultrasonic transmitting unit and the other of the first member and the second member includes an ultrasonic receiving unit.

10. The infusion pump according to claim 1, wherein a display unit and an operation panel are disposed at an upper portion of the main body, and the tube attachment section, the liquid feed driving unit, and the access cover are disposed at a lower portion of the main body.

11. The infusion pump according to claim 1, wherein the infusion tube configured to feed a medicinal solution to a patient side of the infusion pump is attachable in a horizontal direction, and the liquid feed driving unit is configured to feed the medicinal solution inside the infusion tube in the horizontal direction.

* * * * *